United States Patent
Ito et al.

(10) Patent No.: US 6,346,425 B1
(45) Date of Patent: Feb. 12, 2002

(54) VAPOR-PHASE PROCESSING METHOD CAPABLE OF ELIMINATING PARTICLE FORMATION

(75) Inventors: Natsuko Ito; Tsuyoshi Moriya; Fumihiko Uesugi, all of Tokyo; Shuji Moriya, Nirasaki; Masaru Aomori, Nirasaki; Yoshinori Kato, Nirasaki; Mitsuhiro Tachibana, Nirasaki, all of (JP)

(73) Assignees: Tokyo Electron Limited; NEC Corporation, both of Tokyo (JP)

( * ) Notice: Subject to any disclaimer, the term of this patent is extended or adjusted under 35 U.S.C. 154(b) by 0 days.

(21) Appl. No.: 09/651,186

(22) Filed: Aug. 30, 2000

(30) Foreign Application Priority Data

Mar. 3, 2000 (JP) ........................................ 2000-059440

(51) Int. Cl.⁷ .................... H01L 21/00; H01L 21/66; H01L 21/44; H01L 21/31; G01R 31/26
(52) U.S. Cl. ........................ 438/7; 438/16; 438/680; 438/758
(58) Field of Search ................................ 438/758, 800, 438/7, 16, 680, 685; 427/248.1, 585, 588

(56) References Cited

U.S. PATENT DOCUMENTS

| 5,861,951 A | 1/1999 | Useugi et al. | 356/338 |
| 5,870,189 A | 2/1999 | Useugi et al. | 356/335 |
| 6,042,650 A | 3/2000 | Useugi et al. | 118/712 |

FOREIGN PATENT DOCUMENTS

| JP | 6-124902 | 5/1994 |
| JP | 10-10036 | 1/1998 |
| JP | 10-232196 | 9/1998 |
| JP | 10-308333 | 11/1998 |
| JP | 11-44654 | * 2/1999 |

* cited by examiner

*Primary Examiner*—Alexander G. Ghyka
(74) *Attorney, Agent, or Firm*—Pillsbury Winthrop LLP (57) ABSTRACT

A method for processing a substrate includes the steps of determining an allowable margin of process condition such that a substrate is processed without forming particles, selecting a process condition of a substrate for a production process such that the process condition falls in the allowable margin in the production process, and carrying out a processing of the substrate in the production process at the selected process condition, wherein the step of determining the allowable margin includes the steps of introducing an optical beam to an atmosphere in which the substrate is processed in the step of determining the allowable margin, and detecting scattering of the optical beam.

10 Claims, 7 Drawing Sheets

VAPOR-PHASE PROCESSING METHOD CAPABLE OF ELIMINATING PARTICLE FORMATION

BACKGROUND OF THE INVENTION

The present invention generally relates to fabrication of semiconductor devices and more particularly to a vapor-phase processing method and apparatus for use in fabrication process of semiconductor devices.

A CVD process is a typical vapor-phase process used in fabrication process of semiconductor devices for depositing various layers on a substrate. Further, a plasma process such as a dry etching process is another typical example of the vapor-phase process used in the fabrication process of semiconductor devices.

In such a vapor-phase process of a substrate, it is necessary to control the process condition such that formation of particles is eliminated during the vapor-phase process. This requirement of eliminating the particle formation is becoming a particularly acute problem in the case of fabricating advanced, leading-edge semiconductor devices having extremely fine patterns.

Conventionally, control of a vapor-phase process condition has been achieved by detecting the particles that remain on the substrate by examining the substrate surface by way of optical means after the process has been conducted. However, such an optical examination of the substrate surface cannot detect particles having a diameter less than 0.3 $\mu$m, while it is thought that the particles of the diameter less than 0.3 $\mu$m may cause the problem of rough surface in the processed surface. Further, in view of the fact that the process is not a real-time process, there has been a difficulty in grasping the situation of particle formation in the conventional substrate processing method and apparatus.

In view of the situations noted above, there has been a proposal in the Japanese Laid-Open Patent Application No.11-44654 with regard to a substrate processing apparatus that enables a real-time detection of particle formation.

Figure 1:
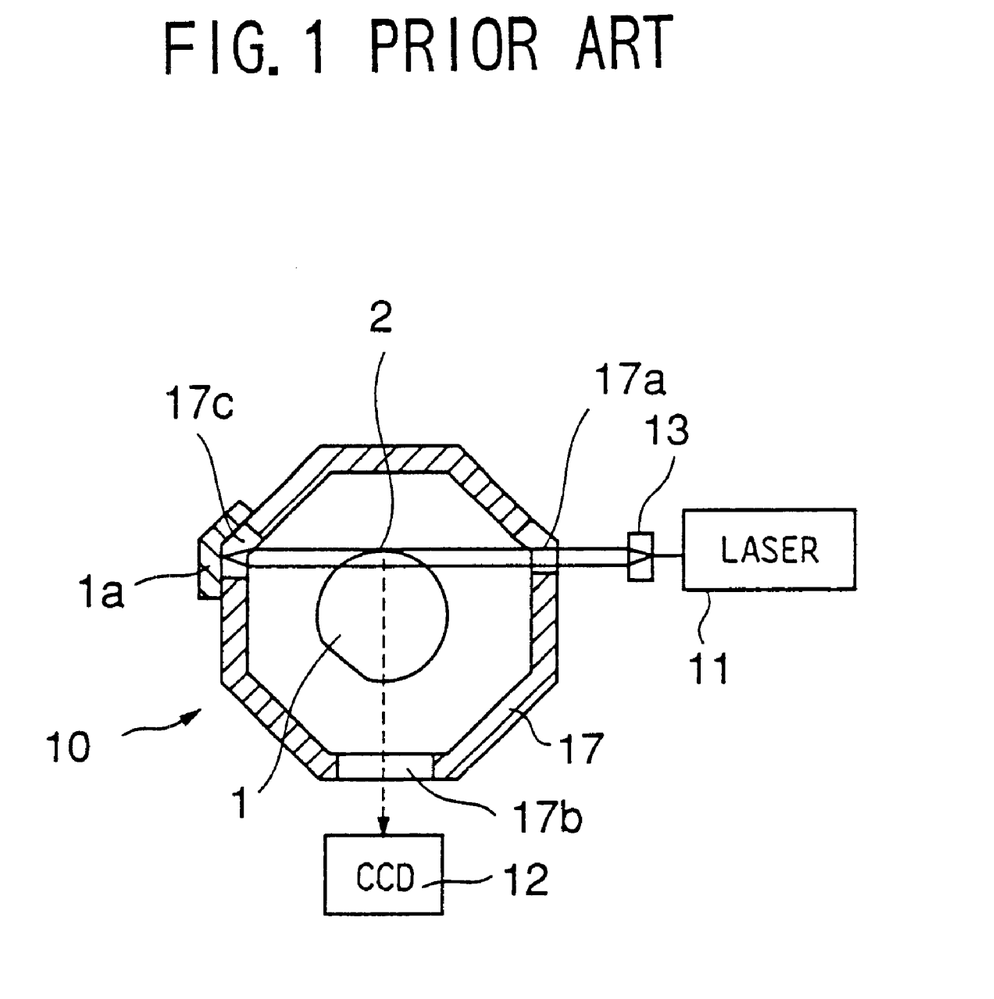
FIG. 1 is a diagram showing the construction of a conventional processing apparatus.

FIG. 1 shows the construction of a conventional substrate processing apparatus 10 disclosed in the foregoing Japanese Laid-Open Patent Application No.11-44654.

Referring to FIG. 1, the substrate processing apparatus 10 includes a reaction chamber 17 accommodating therein a semiconductor substrate 1 for processing, and a laser beam source 11 that produces a laser beam is provided such that laser beam is injected into the reaction chamber 17. Further, an optical detector 12 is provided for detecting a scattering of the laser beam caused by particles 2 that are formed in the reaction chamber 17 during a vapor-phase processing conducted therein.

More specifically, the reaction chamber 17 has a first optical window 17a for introducing the laser beam into the reaction chamber 17 from the laser beam source 11 and a second optical window 17c is provided such that the laser beam exits through the second optical window 17b after traveling through the reaction chamber 17. Further, the reaction chamber 17 has a third optical window 17b that allows the scattered laser beam to exit from the reaction chamber 17 after being scattered by the particles 2.

Adjacent to the optical window 17a, there is provided a collimating optical system 13 in alignment with the laser beam source 11, and the laser beam of the laser beam source 11 is injected into the optical window 17a via the foregoing optical system 13. The optical detector 12, in turn, is provided adjacent to the optical window 17b and detects the scattered laser beam that has exited from the reaction chamber 17 through the optical window 17b. Further, a beam damper 18 is disposed adjacent to the optical window 17c at the outer side of the reaction chamber 17 so as to absorb the optical beam that has exited the reaction chamber 17 through the optical window 17b.

In the processing apparatus 10 of FIG. 1, it becomes possible to detect the formation of the particles 2 in the reaction chamber 17 real time, in other words, during the process of depositing a film, by monitoring the scattering of the laser beam by means of the optical detector 12. The film thus formed may be a metal film such as a W film. By setting the optical path of the laser beam such that the laser beam passes a limited region above the substrate 1 in which the probability of particle formation is maximum, it becomes possible to minimize the particle formation in the reaction chamber 17 during the process applied to the substrate 1.

While the prior art processing apparatus 10 of FIG. 1 is thus capable of detecting the formation of particles in real time, there is a drawback in that the apparatus 10 requires a bulky laser beam source 11 and cooperating optical system 13. Further, the processing apparatus 10 requires the optical detector 12. Thus, there arises a problem, particularly when the processing apparatus 10 of FIG. 1 is used to construct a single-wafer processing system or cluster-type wafer processing system together with other various substrate processing apparatuses, in that the space necessary for accommodating the substrate processing apparatus 10 may not be available. Further, the laser beam source 11, typically formed of a YAG laser for producing the laser beam with several watts of output power, or the optical detector 12 typically formed of a high-sensitivity CCD camera for high-sensitivity detection of laser beam scattering, is extremely expensive and increases the fabrication cost of the semiconductor device.

Thus, there has been a difficulty to use the processing apparatus 10 of FIG. 1 for mass production of semiconductor devices.

SUMMARY OF THE INVENTION

Accordingly, it is a general object of the present invention to provide a novel and useful processing method of substrate wherein the foregoing problems are eliminated.

Another and more specific object of the present invention is to provide a processing method of a substrate with minimized particle formation.

Another object of the present invention is to provide a method for processing a substrate, comprising the steps of:
  (a) determining an allowable margin of processing condition in which a substrate is processed without forming particles;
  (b) selecting a processing condition such that said processing condition falls in said allowable margin; and
  (c) carrying out a processing of a substrate at said selected processing condition, said step (a) for determining said allowable margin comprising the steps of:
    (a1) setting a process condition;
    (a2) introducing an optical beam to an atmosphere in which said substrate is processed;
    (a3) carrying out a processing of said substrate in said atmosphere;
    (a4) detecting a scattering of said optical beam; and
    (a5) changing said processing condition.

According to the present invention, it is possible to fabricate a semiconductor device efficiently by first determining the allowable margin of process condition in the step (a) and then setting the process condition within the allowable process margin in the steps (b) and (c). By using different processing apparatuses for the step (a) and for the steps (b) and (c), it is possible to eliminate the optical beam source or the optical detector for detecting the scattered optical beam in the processing apparatus used in the steps (b) and (c) for mass-producing semiconductor devices. According to such a construction, the processing apparatus used for the steps (b) and (c) has a simplified construction and a compact size, and thus, can be used to construct a single-wafer processing system together with other various processing apparatuses. According to the present invention, it becomes possible to control the formation of ultrafine particles having a particle diameter of several-ten nanometers or less, of which control has been difficult when conventional particle monitor devices are used.

Other objects and further features of the present invention will become apparent from the following detailed description when read in conjunction with the attached drawings.

DETAILED DESCRIPTION OF THE PREFERRED EMBODIMENTS

Figure 2:
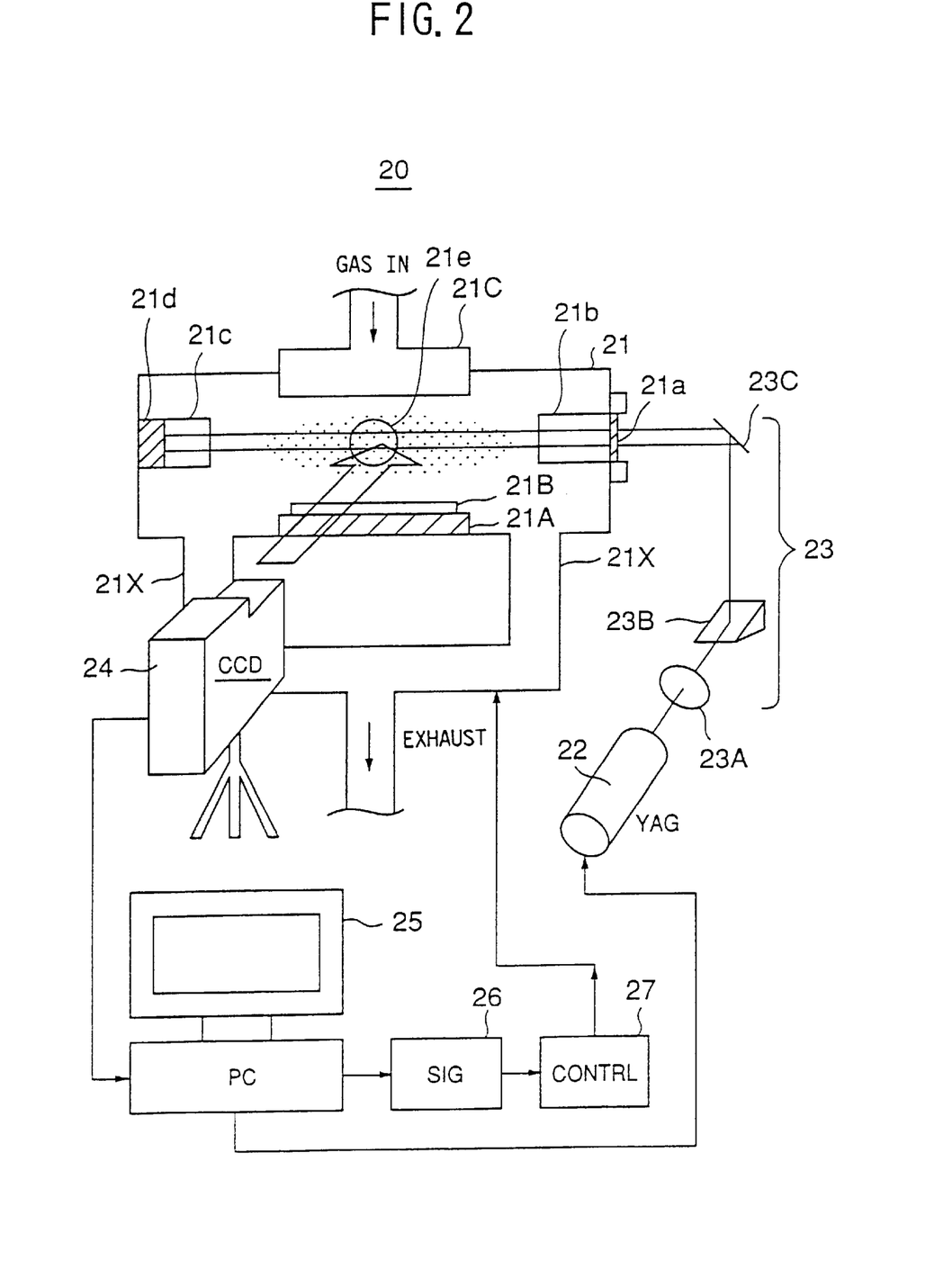
FIG. 2 is a diagram showing the construction of a processing apparatus used in the present invention for determining an allowable margin of process condition.

FIG. 2 shows the construction of a processing apparatus 20 used in the present invention.

Referring to FIG. 2, the processing apparatus 20 is a CVD apparatus and includes a reaction chamber 21 evacuated at an evacuation port 21X. The reaction chamber 21 accommodates therein a substrate holder 21A for holding a substrate 21B to be processed, and a showerhead 21C is provided also in the reaction chamber 21 so as to face the substrate 21B on the substrate holder 21A, for introducing a source gas or a combination of source gases.

Adjacent to the reaction chamber 21, the processing apparatus 20 includes a YAG laser as an optical source 22, wherein the YAG laser 22 produces an optical beam having a wavelength of 532 nm in the form of a second harmonic wave. In cooperation with the YAG laser 22, there is provided an optical system 23, wherein the optical system 23 includes a collimator lens 23A, mirrors 23B and 23C, and the like. Thus, the optical beam produced by the YAG laser 22 is introduced into the reaction chamber 21 via an optical window 21a provided on the reaction chamber 21 after being directed by the optical system In the reaction chamber 21, there is provided a slit 21b adjacent to the optical window 21a, and the slit 21b shapes the laser beam thus introduced into the reaction chamber 21 to have a flat cross-sectional shape. The laser beam thus shaped then travels through the reaction chamber 21 along an optical path that is located at a position about 6 mm upward from the surface of the substrate 21B and hits a damper 21d provided at an opposite side of the reaction chamber 21 after passing through a cooperating slit 21c. The damper 21d thereby absorbs the laser beam incident thereto.

Further, it should be noted that the reaction chamber 21 carries an optical window 21e at a location offset from the optical path of the incident laser beam, and a CCD camera 24 is disposed outside the reaction chamber 21 so as to monitor the formation of particles or particle cloud in the reaction chamber 21 through the optical window 21e. It should be noted that the CCD camera 24 carries out an in-situ observation of the particle formation in the reaction chamber 21 and produces an output signal representing a two-dimensional movie image of the particle cloud formation. The output image signal of the CCD camera 24 is then forwarded to an image processing unit 25, which may be a personal computer, for image processing.

The image processing unit 25 then processes the two-dimensional image and supplies an output image signal to a signal processing unit 26, wherein the signal processing unit 26 detects the occurrence of particle formation in the reaction chamber 21 by applying a threshold process to the number of the scattering events recorded in the two-dimensional image signal of the processing unit 25. The threshold of the signal processing unit 26 determines the sensitivity of particle detection and may be set as desired in view of the necessary sensitivity of particle detection, which is related to the allowable particle diameter. The output of the signal processing unit 26 is further supplied to a control unit 27 and the control unit 27 controls the overall operation of the CVD apparatus 20 based on the output signal of the signal processing unit 26. As represented in FIG. 2, the control unit 27 controls the YAG laser 22, and the YAG laser 22 produces output optical pulses of several watts, typically 2.5 W, with a repetition frequency of 10 kHz, for example.

According to such a construction, it is possible for the CCD camera 24 to detect the formation of particles having a diameter larger than 10 nm, provided that the camera gain is set properly. Further, it is possible for the CCD camera 24 to detect the particles of even smaller diameter in the form of particle cloud, provided that the density of the particle cloud is sufficiently large.

In the apparatus 20 of FIG. 2, it is also possible to set the sensitivity of particle detection as desired by adjusting the output power of the YAG laser 22 in correspondence to the allowable particle diameter.

First Embodiment

Next, the process steps for determining the allowable margin of process condition according to a first embodiment of the present invention will be described with reference to the flowchart of FIG. 3.

In the present embodiment, a description will be given for the case of depositing a W film on the substrate 21B by a pyrolytic CVD process in which $WF_6$ and $SiH_4$ are supplied to the reaction chamber 21 via the showerhead 21C.

Figure 3:
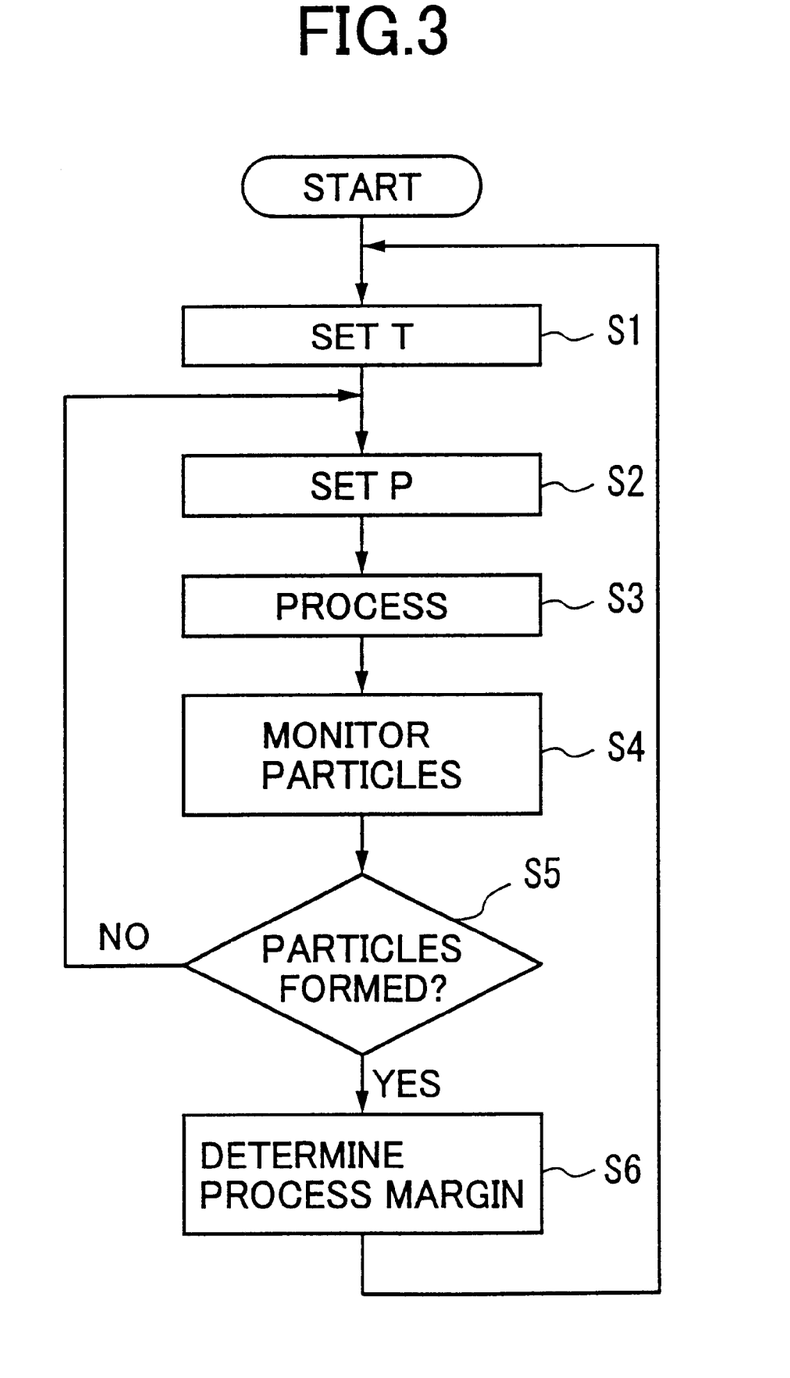
FIG. 3 is a flowchart showing the process steps for determining an allowable margin of process condition using the apparatus of FIG. 2 according to a first embodiment of the present invention.

Referring to FIG. 3, the present embodiment determines the allowable margin of process condition with regard to the internal pressure of the reaction chamber 21, such that no particle formation occurs during the process of depositing the W film, while changing the internal pressure of the reaction chamber 21 variously.

More specifically, the process of FIG. 3 starts with a step S1 in which the temperature of the substrate 21B is set to a predetermined temperature and a step S2 is conducted in which the internal pressure of the reaction chamber 21 is set to a predetermined initial value.

Next, the deposition of a W film is conducted on the substrate 21B in the next step S3 under the condition set in the foregoing steps S1 and S2.

While conducting the deposition process in the step S3, a step S4 is conducted in which the interior of the reaction chamber 21 is monitored by the CCD camera 24 for any occurrence of scattering of the incident laser beam.

After the step S4, a step S5 is conducted in which the occurrence or no-occurrence of particle formation is judged based on the result of the image processing applied to the two-dimensional image signal produced by the CCD camera 24 by the image processing unit 25. When there is no particle occurrence detected, the process returns to the process step S2 and the internal pressure of the reaction chamber 21 is changed.

By repeating the process steps S1–S4 until the formation of particles is detected in the step S5, an allowable margin of process condition is obtained in the step S6 with regard to the internal pressure of the reaction chamber 41 for the temperature set at the step S1.

After the step S6, the process returns to the process step S1 and the substrate temperature is changed. Further, by repeating the steps S1–S6, the allowable margin of process condition is determined for the substrate temperature and the internal pressure. The table below summarizes the result of the experiments for observing particle occurrence conducted at the substrate temperature of 460° C. or 410° C. while changing the internal pressure of the reaction vessel from 1.3–3.3 kPa (10–25 Torr) with a step of 0.67 kPa (5 Torr).

TABLE I

| pressure (Torr) | 460° C. $WF_6/SiH_4 = 15/4$ | 410° C. $WF_6/SiH_4 = 15/4$ |
| --- | --- | --- |
| 10 | o | — |
| 15 | o | o |
| 20 | x | o |
| 25 | x | x | o no particle observed
x particle observed

Referring to TABLE I, the experiments were conducted at 460° C. and 410° C. while supplying $WF_6$ and $SiH_4$ with respective flow-rates of 15 SCCM and 4 SCCM, wherein it can be seen that a particle formation is observed at the substrate temperature of 460° C. when the internal pressure of the reaction chamber 21 has reached a value of 20 Torr or 2.7 kPa. In the case the substrate temperature is set to 410° C., on the other hand, it can be seen that a particle formation is observed when the internal pressure has reached a value of 25 Torr or 3.8 kPa.

From the result of TABLE I, the preferable process condition in which a deposition is achieved without substantial particle formation, or "allowable margin of the process condition," is determined to be 15 Torr (2.0 kPa) or less when the substrate temperature is 460° C. or 20 Torr (2.7 kPa) or less when the substrate temperature is 410° C. for the pyrolytic CVD process of W film that uses $WF_6$ and $SH_4$ source gases.

In the foregoing experiments, attempt was also made to detect the formation of particles by using a conventional particle monitor device having a sensitivity of particle detection for the particles having a diameter of 0.2 μm or more. It turned out that no particle detection was made by the particle monitor device in any of the experiments conducted at the substrate temperature of 460° C. or 410° C., indicating that the particles detected by the apparatus 20 of FIG. 2 and represented in the TABLE I have a diameter well below the threshold of particle detection of the conventional particle monitor device.

Further, a microscopic examination was made on the substrates obtained in the foregoing CVD experiments for the particles having a diameter of 0.2 μm or more. It turned out that the number of the particles is less than 100 for any of those substrates represented in TABLE I as having particles and those substrates represented in TABLE I as not having particles. This result of the optical examination indicates that the particles detected in the foregoing experiments by using the processing apparatus 20 of FIG. 2 are ultrafine particles which cannot be detected by conventional particle monitors or microscopic examination. As explained previously, the processing apparatus 20 of FIG. 2, which uses the CCD camera 24 for the particle detection, can detect the particles having a diameter of larger than about 10 nm, more specifically larger than 14 nm, when the gain of the CCD camera 24 is set properly. Further, the sensitivity or resolution of particle detection can be set as desired by adjusting the output power of the laser 22.

It should be noted that the foregoing determination of the allowable margin of process condition by using the processing apparatus 20 of FIG. 2 for the in-situ observation of particle formation is by no means limited to the pyrolytic CVD process of a W film but is applicable to any vapor phase deposition process including plasma CVD process for depositing various films such as conductor films other than the W film or semiconductor films or insulating films.

In the construction of FIG. 2 that uses the YAG laser 22 having the wavelength of 532 nm for the optical source, the problem of interference of the laser beam with the optical radiation caused by plasma is successfully avoided. Thus, the construction of FIG. 2 can be used also in the plasma CVD process. Further, the determination process of the allowable margin of process condition according to the present invention is applicable also to a plasma etching process and apparatuses.

Further, the process condition as used in the present invention is not limited to the substrate temperature or internal pressure of the reaction chamber as noted above, but also includes the flow-rate or flow-rate ratio of various gases used in the processing, or the plasma power in the case of a plasma processing apparatus.

Second Embodiment

As noted above, the substrate processing apparatus 20 of FIG. 2 can detect the formation of extremely fine particles with high-sensitivity. On the other hand, the apparatus 20 of FIG. 2 needs a considerable space for accommodating the YAG laser 22 and the cooperating optical system 23 in the vicinity of the reaction chamber 21. Further, there is a need in the apparatus 20 of FIG. 2 to secure a space also for the CCD camera 24 in the vicinity of the reaction chamber 21.

In the case of the processing apparatus for use in a production line of semiconductor devices, a typical example of which may be the single-wafer processing system or so-called cluster-type system, there frequently occurs the situation in which such a space is not available. Further, in view of the high cost of the expensive high-power YAG laser 22 and the cooperating optical system 23 or the high cost of the expensive CCD camera 24 and the cooperating image processing system 25, it is not practical to use the construction of the processing apparatus 20 of FIG. 2 in the mass-production line of semiconductor devices.

Figure 4:
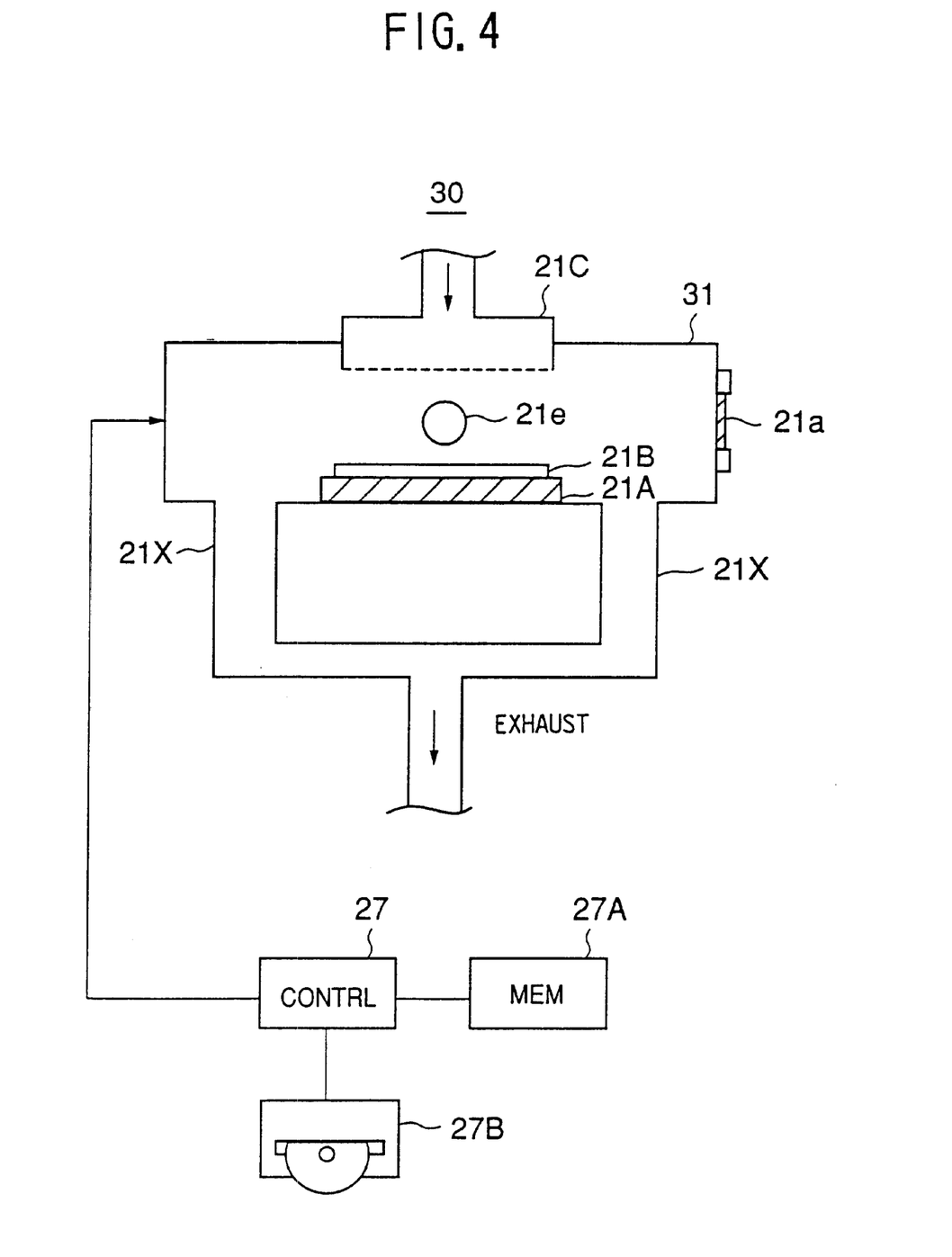
FIG. 4 is a diagram showing the construction of a processing apparatus used in the present invention for mass-producing semiconductor devices.

Thus, the present embodiment provides a processing apparatus 30 represented in FIG. 4 for use in the mass-production line of semiconductor devices, wherein the processing apparatus 30 has substantially the same construction to the processing apparatus 20 of FIG. 2, except that the YAG laser 22, the optical system 23, the CCD camera 24 and the processing units 25 and 26 are omitted. In FIG. 4, it should be noted that those parts corresponding to the parts described previously with reference to FIG. 2 are designated by the same reference numerals and the description thereof will be omitted.

Referring to FIG. 4, the processing apparatus 30 uses a reaction chamber 31 in place of the reaction chamber 21 of the apparatus 20 of FIG. 2, wherein the reaction chamber 31 has a construction similar to that of the reaction chamber 21 except that the slits 21b and 21c and the beam damper 21d are omitted. Otherwise, the reaction chamber 31 is identical with the reaction chamber 21. In the reaction chamber 31, it is possible to eliminate the observation windows 21a and 21b.

In the processing apparatus 30 of FIG. 4, it should be noted that the processing reaction taking place in the reaction chamber 31 is controlled by the controller 27 similarly to the processing apparatus 20, wherein it should be noted that the controller 27 of the processing apparatus 30 has a storage unit 27A for holding the allowable process margin of the process condition obtained in the processing apparatus 20 of FIG. 2 in the form of a database. Further, the controller 27 has an input device 27B for writing the allowable margin of the process conduction into the storage unit 27A. The writing of the allowable margin of process condition from the input device 27B to the storage unit 27A may be carried out by way of a medium such as a magnetic or optical disk or manually by using a keyboard. Alternatively, the writing of the allowable margin may be conducted by way of a telecommunication network.

It should be noted that such a writing of the allowable margin of process condition may be conducted at the time of delivering the processing apparatus 30 from the manufacturer to a user, but the database of the allowable margin may be updated later as desired.

Figure 5:
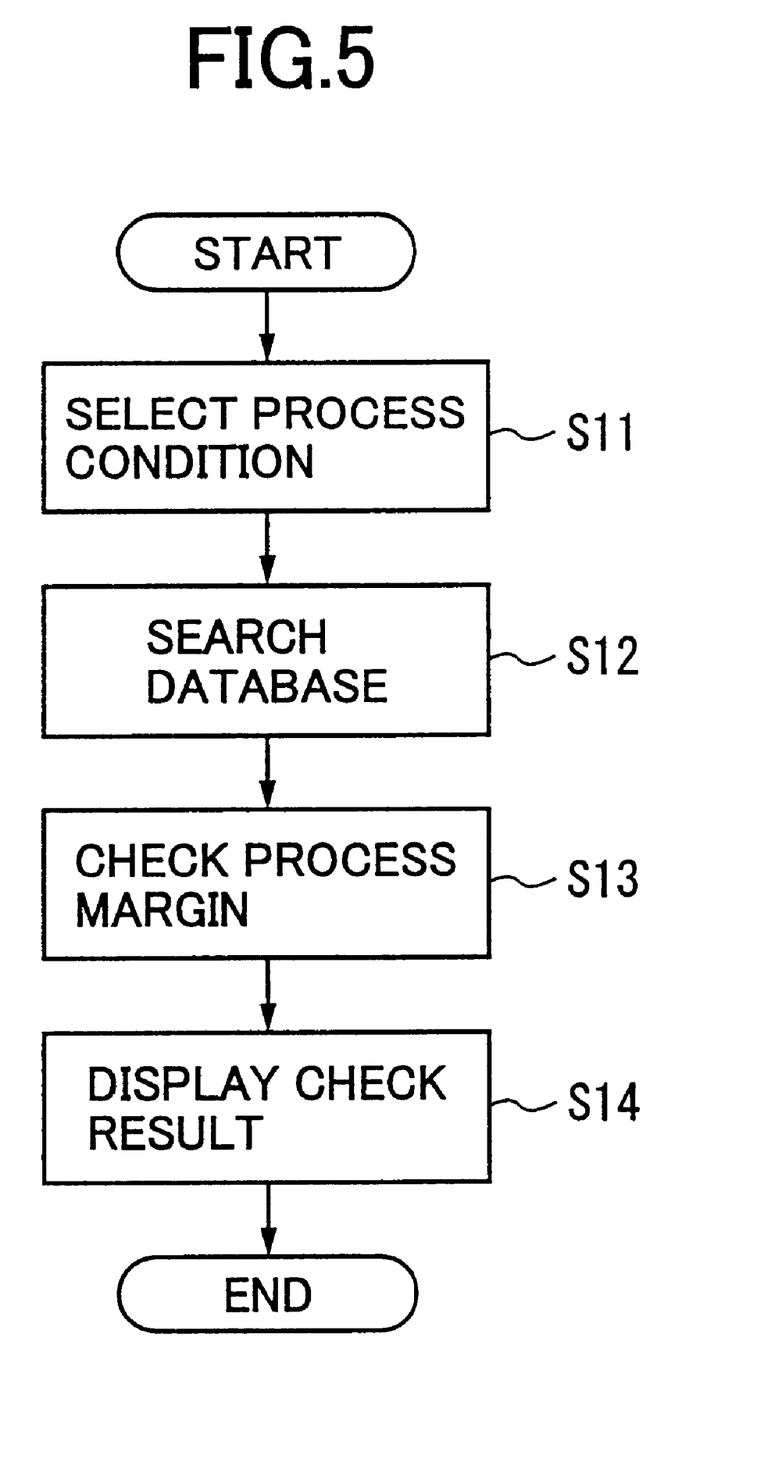
FIG. 5 is a flowchart showing a mass-production process of semiconductor devices using the processing apparatus of FIG. 4 according to a second embodiment of the present invention.

FIG. 5 shows the flowchart of the process used in the production process conducted by the processing apparatus 30 for setting the process condition.

Referring to FIG. 5, the process starts with a step S11 wherein process parameters such as the substrate temperature, internal pressure of the reaction chamber 31 and the reaction gases used for the substrate processing are selected for the given process, and a step S12 is conducted subsequently wherein a search is made in the database held in the storage unit 27A for the specified combination of the process parameters. Further, a step S13 is conducted in which a judgment is made whether or not the selected combination of the specified parameters falls in the allowable margin of the process condition. The result of the judgment of the step S13 is displayed in the next step S14.

Figure 6:
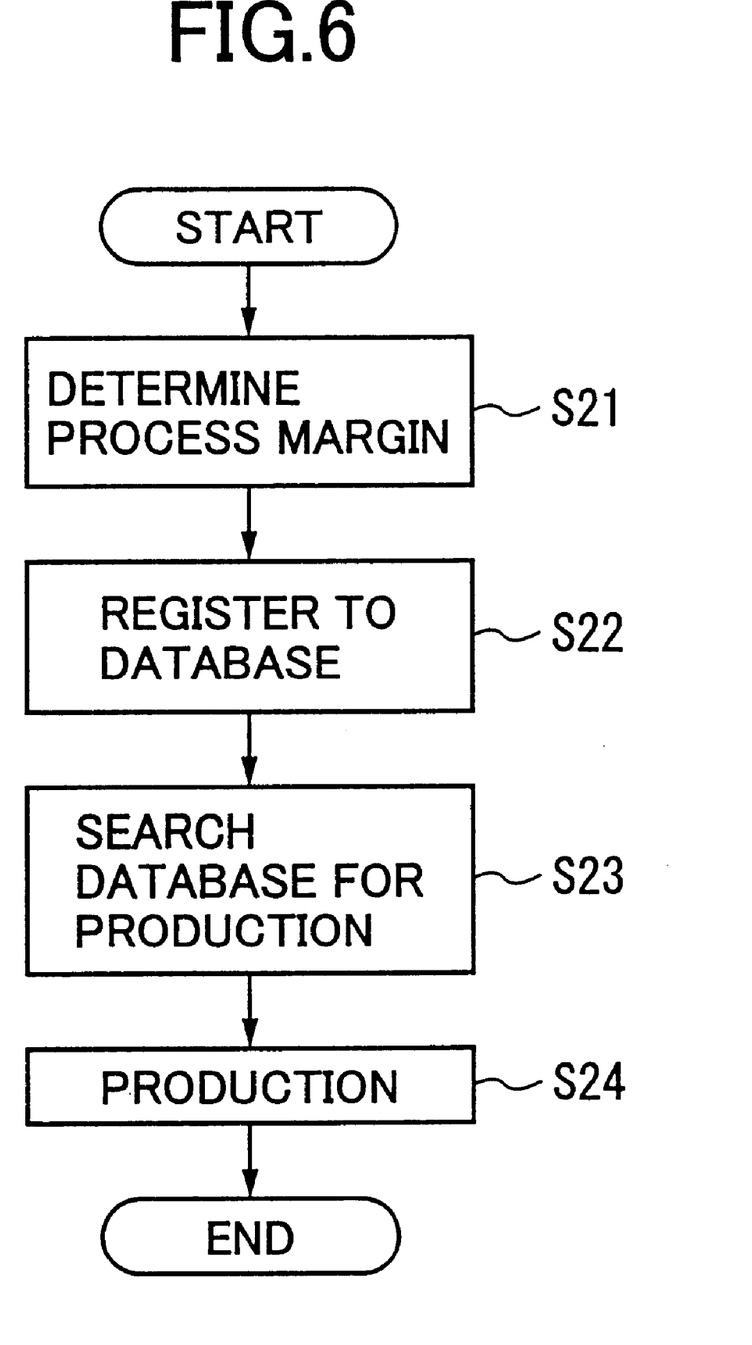
FIG. 6 is a flowchart showing the mass-production process of semiconductor devices using the processing apparatuses of FIG. 4, wherein the flowchart of FIG. 6 includes the process steps for determining the allowable margin process condition.

FIG. 6 shows the overall flowchart of the processing conducted in the processing apparatus 20 of FIG. 2 and the processing apparatus 30 of FIG. 4.

Referring to FIG. 6, the process starts with a step S21 in which the process of FIG. 3 is conducted by using the processing apparatus 20 of FIG. 2 and the allowable margin of process condition is obtained.

Next, in the step S22, the allowable margin of process condition is registered to the database held in the memory device 27A of the processing apparatus 30 of FIG. 4. Thus, the process steps S21 and S22 correspond to the preparation step of the semiconductor fabrication process conducted by the processing apparatus 30 of FIG. 4.

Next, a mass production of semiconductor devices is started with the step S23 wherein the database is searched for the process condition to be used. Upon confirmation that selected process condition falls in the allowable margin of the process condition, the mass production process is conducted in the step S24.

Third Embodiment

In the embodiments described heretofore, the allowable margin was obtained for the process condition such as substrate temperature, internal pressure of the reaction chamber, various gas flow-rates or flow-rate ratio, or plasma power. On the other hand, the allowable margin thus obtained for various process parameters may change with time. The present invention also provides a way to determine the allowable margin with regard to the aging of the process condition or the aging of the allowable margin of process condition determined previously.

Figure 7:
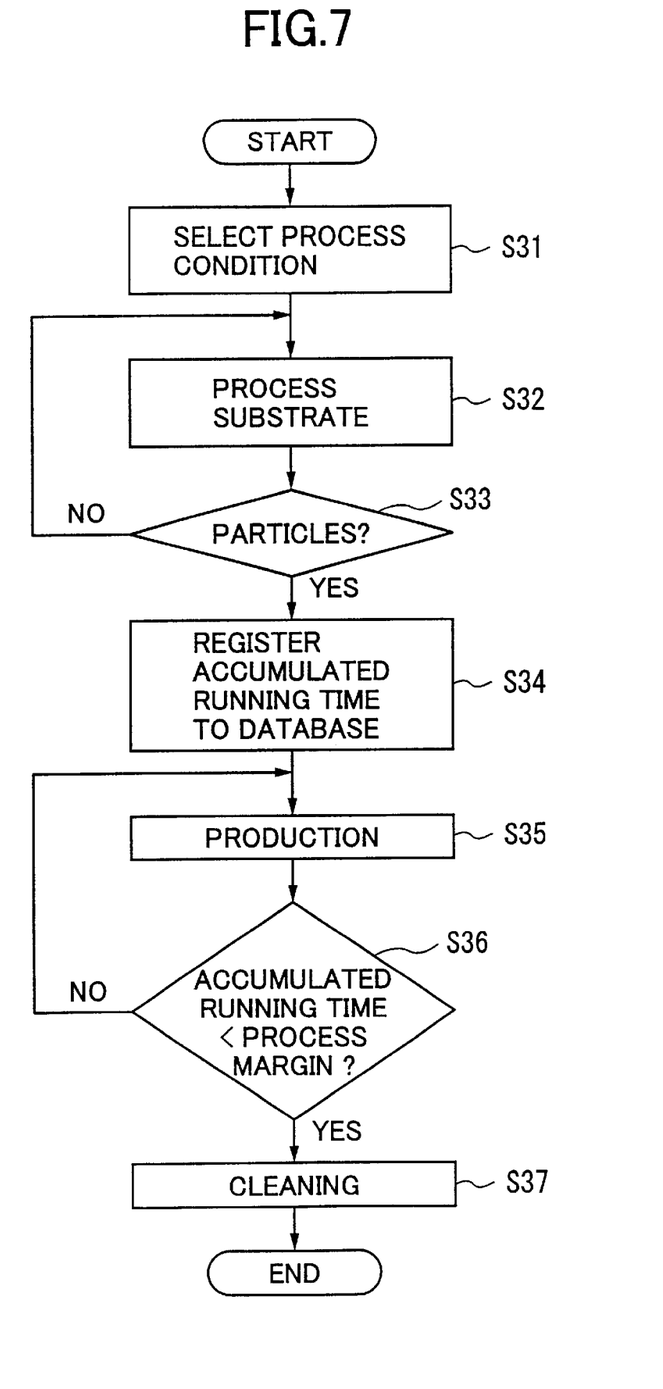
FIG. 7 is a flowchart showing a mass-production process of semiconductor devices that controls an accumulated running time of a processing apparatus within an allowable margin.

FIG. 7 shows an example of the flowchart used for determining the allowable margin for the aging of the process condition.

Referring to FIG. 7, the process starts with a step S31 in which the processing apparatus 20 of FIG. 2 is used and the process condition of the processing apparatus 20 is set so as to fall in the process margin determined previously by the process of FIG. 3.

Next, in the step S32, a deposition of a film such as a W film is conducted repeatedly at the process condition set in the step S31 while replacing the substrate. Each time the deposition is made in the step S32, a step S33 for monitoring the occurrence of particles in the reaction chamber 21 is conducted by using the optical source 22 and the CCD camera 24. When the occurrence of particles is detected, the accumulated running time of the processing apparatus 20 is calculated, and the accumulated running time thus calculated is registered to the database.

Next, a step 35 for mass-producing the semiconductor devices is conducted repeatedly by using the processing apparatus 30 of FIG. 4 as noted previously, wherein the accumulation time of processing is calculated each time the process of the step S35 is conducted and compared in the step S36 with the accumulated running time registered in the database held in the storage unit 27A.

When it is discriminated in the step S36 that the accumulation time thus obtained has reached the accumulated running time registered in the database, the control unit 27 of the processing apparatus 30 switches the operation mode of the processing apparatus 30 in the step S37 to a cleaning mode and the interior of the reaction chamber 31 and further the lines connected thereto are cleaned.

According to the present embodiment, cleaning process is conducted timely based on the accumulated running time held in the storage unit 27A, and the particle formation is eliminated in the device fabrication process even when the processing apparatus 30 is operated for a long time. At the same time, unnecessary cleaning process is eliminated. Thereby, the efficiency of running the processing apparatus 30 is maximized.

In any of the embodiments described heretofore, it should be noted that particles having a diameter of several tens of nanometers or less, which are hitherto not detectable by the conventional particle monitor devices, are successfully detected, and the defect formation caused by such ultrafine particles, such as the formation of rough surface, is effectively eliminated from the surface of various layers formed on a substrate including semiconductor layers, conductor layers or insulating layers. Thus, the present invention is useful and effective for improving the yield of ultrafine semiconductor devices such as the one called sub-half micron devices or sub-quarter micron devices.

Further, the present invention is not limited to the embodiments described heretofore, but various variations and modifications may be made without departing from the scope of the invention.

The present invention is based on the Japanese patent application 2000-059440 filed mar. 3, 2000, the entire contents thereof is incorporated herein as reference.

What is claimed is:

1. A method for processing a substrate, comprising:
   (a) determining an allowable margin of process condition in which a substrate is processed in a first vessel without forming particles;
   (b) selecting a process condition such that said process condition falls in said allowable margin; and
   (c) carrying out a processing of a substrate at said selected process condition in a second vessel,
   said (a) determining said allowable margin comprising:
      (a1) selecting a process condition;
      (a2) introducing an optical beam to an atmosphere in which said substrate is processed for determining said allowable margin;
      (a3) carrying out a process of said substrate in said atmosphere;
      (a4) detecting a scattering of said optical beam; and
      (a5) changing said process condition.

2. A method as claimed in claim 1,
   wherein said (a) determining further comprises (a6) determining said allowable margin of process condition based on a result of said (a4) detecting such that no substantial scattering of said optical beam is observed in said allowable margin of process condition.

3. A method as claimed in claim 2,
   wherein said (a5) changing includes changing-a pressure as said process condition, and
   wherein said (a6) determining includes determining said allowable margin as a range of pressure in which no substantial scattering of said optical beam is observed in said (a4) detecting.

4. A method as claimed in claim 2,
   wherein said (a5) changing includes changing a substrate temperature as said process condition, and
   wherein said (a6) determining includes determining said allowable margin as a range of substrate temperature in which no substantial scattering of said optical beam is observed in said (a4) detecting.

5. A method as claimed in claim 2,
   wherein said (a5) changing includes changing a gas flow rate as said process condition, and wherein said (a6) determining includes determining said allowable margin as a range of gas flow rate in which no substantial scattering of said optical beam is observed in said (a4) detecting.

6. A method as claimed in claim 2,
   wherein said (a5) changing includes changing an accumulated running time of carrying out of said (a3) process, and wherein said (a6) determining includes determining said allowable margin as a range of said accumulated running time in which no substantial scattering of said optical beam is observed in said (a4) detecting.

7. A method as claimed in claim 6, wherein said (c) carrying out farther comprises carrying out a cleaning process when an accumulated running time of said process has exceeded said allowable margin of process condition.

8. A method as claimed in claim 1,
   wherein said (a3) carrying out and said (c) carrying out comprise a pyrolytic CVD process of W.

9. A method as claimed in claim 1,
   wherein said (a2) introducing further comprises setting an intensity of said optical beam in response to an allowable size of particles in said atmosphere.

10. A method as claimed in claim 1,
    wherein said (a4) detecting comprises a threshold process applied to a number of counts of said scattering.

* * * * *